United States Patent
Cook

(10) Patent No.: US 10,485,558 B1
(45) Date of Patent: Nov. 26, 2019

(54) APPARATUS AND METHOD FOR HARVESTING BONE

(71) Applicant: Joshua Cook, Fruit Heights, UT (US)

(72) Inventor: Joshua Cook, Fruit Heights, UT (US)

(*) Notice: Subject to any disclaimer, the term of this patent is extended or adjusted under 35 U.S.C. 154(b) by 485 days.

(21) Appl. No.: 15/225,409

(22) Filed: Aug. 1, 2016

Related U.S. Application Data

(60) Provisional application No. 62/199,891, filed on Jul. 31, 2015.

(51) Int. Cl.
| | | |
|---|---|---|
| *A61B 17/16* | (2006.01) |
| *A61B 10/02* | (2006.01) |
| *A61B 90/00* | (2016.01) |
| *A61B 17/00* | (2006.01) |
| *A61F 2/46* | (2006.01) |

(52) U.S. Cl.
CPC ........ *A61B 17/1635* (2013.01); *A61B 10/025* (2013.01); *A61B 17/1637* (2013.01); *A61B 90/06* (2016.02); *A61B 2017/00433* (2013.01); *A61B 2090/062* (2016.02); *A61B 2217/00* (2013.01); *A61F 2/4603* (2013.01); *A61F 2002/4619* (2013.01); *A61F 2002/4681* (2013.01)

(58) Field of Classification Search
CPC .............. A61B 17/1635; A61B 10/025; A61B 17/1637; A61F 2002/4619; A61F 2002/4681
USPC ....................................................... 606/100
See application file for complete search history.

(56) References Cited

U.S. PATENT DOCUMENTS

| | | | | |
|---|---|---|---|---|
| 3,334,624 A * | 8/1967 | Schneider | ............ | A61B 17/921 254/20 |
| 3,892,232 A * | 7/1975 | Neufeld | ............... | A61B 17/742 606/104 |
| 4,222,382 A * | 9/1980 | Antonsson | ............ | A61F 2/4607 606/100 |
| 4,399,813 A * | 8/1983 | Barber | ............... | A61B 17/1615 606/100 |
| 4,476,861 A * | 10/1984 | Dimakos | ................ | A61B 17/92 29/255 |

(Continued)

FOREIGN PATENT DOCUMENTS

| | | |
|---|---|---|
| EP | 824893 B1 | 11/2005 |
| EP | 1641379 B1 | 8/2010 |

(Continued)

*Primary Examiner* — David W Bates
(74) *Attorney, Agent, or Firm* — David Meibos; Maywood IP Law

(57) ABSTRACT

A bone harvesting device may facilitate the removal of bone from a surgical site, for therapeutic or diagnostic purposes. The device may have a harvester tube, a harvester tube fitting, and a slide hammer. The harvester tube may have a proximal end, a distal end, and a hollow portion that can receive a sample of the bone and/or a plunger with a point that breaches cortical bone. The harvester tube fitting may be coupled to the proximal end of the harvester tube, and may receive impact to urge the distal end of the harvester tube into the bone. The slide hammer may translate along the harvester tube and impact the harvester tube fitting to urge removal of the proximal end from the bone. Complementary attachment features on the harvester tube fitting and the slide hammer may detachably couple the slide hammer to the harvester tube fitting.

20 Claims, 8 Drawing Sheets

(56) References Cited

U.S. PATENT DOCUMENTS

| | | | | |
|---|---|---|---|---|
| 4,649,918 A * | 3/1987 | Pegg | A61B 17/1637 | 600/567 |
| 4,696,308 A * | 9/1987 | Meller | A61B 10/025 | 408/204 |
| 4,782,833 A * | 11/1988 | Einhorn | A61B 10/025 | 606/80 |
| 4,798,213 A * | 1/1989 | Doppelt | A61B 10/025 | 30/174 |
| 5,049,150 A * | 9/1991 | Cozad | A61B 17/8866 | 606/80 |
| 5,122,143 A * | 6/1992 | McColl | A61B 17/8847 | 606/100 |
| 5,152,792 A * | 10/1992 | Watkins | A61B 17/8847 | 606/87 |
| 5,190,551 A * | 3/1993 | Chin | A61B 17/8847 | 606/100 |
| 5,197,967 A * | 3/1993 | Wilson | A61B 17/1637 | 606/79 |
| 5,476,467 A * | 12/1995 | Benoist | A61B 17/92 | 606/100 |
| 5,562,447 A * | 10/1996 | Moy | A61C 3/14 | 433/150 |
| 5,788,701 A * | 8/1998 | McCue | A61B 17/1604 | 606/86 R |
| 5,800,440 A * | 9/1998 | Stead | A61B 17/1697 | 606/104 |
| 5,913,860 A * | 6/1999 | Scholl | A61B 17/921 | 606/100 |
| 5,928,238 A * | 7/1999 | Scarborough | A61B 17/1637 | 408/201 |
| 5,954,671 A * | 9/1999 | O'Neill | A61B 17/1637 | 600/567 |
| 6,139,509 A | 10/2000 | Yuan et al. | | |
| 6,451,023 B1 * | 9/2002 | Salazar | A61B 17/1637 | 606/79 |
| 6,592,588 B1 * | 7/2003 | Bobic | A61B 10/025 | 600/567 |
| 6,652,533 B2 * | 11/2003 | O'Neil | A61F 2/4611 | 606/100 |
| 6,767,354 B2 | 7/2004 | Johanson | | |
| 6,849,051 B2 | 2/2005 | Sramek et al. | | |
| 7,081,123 B2 | 7/2006 | Merboth et al. | | |
| RE40,796 E | 6/2009 | O'Neill | | |
| 8,043,291 B2 | 10/2011 | Accordino | | |
| 8,162,967 B1 * | 4/2012 | Kaiser | A61B 17/1604 | 279/82 |
| 8,303,662 B2 | 11/2012 | Landry et al. | | |
| 8,764,753 B2 | 7/2014 | Oren et al. | | |
| 9,254,159 B2 * | 2/2016 | Li | A61B 17/8866 | |
| 2003/0083668 A1 * | 5/2003 | Rogers | A61B 17/88 | 606/100 |
| 2005/0240197 A1 * | 10/2005 | Kmiec, Jr. | A61B 17/921 | 606/100 |
| 2006/0178673 A1 * | 8/2006 | Curran | A61B 17/92 | 606/100 |
| 2006/0241647 A1 * | 10/2006 | Chen | B25D 1/00 | 606/100 |
| 2009/0112219 A1 * | 4/2009 | Daniels | A61F 2/4607 | 606/99 |
| 2009/0209964 A1 * | 8/2009 | Yeung | A61B 17/1635 | 606/87 |
| 2010/0331851 A1 * | 12/2010 | Huene | A61B 17/92 | 606/100 |
| 2011/0022053 A1 * | 1/2011 | Schlueter | A61F 2/389 | 606/100 |
| 2012/0302839 A1 | 11/2012 | Marino | | |
| 2015/0025534 A1 | 1/2015 | Gordon et al. | | |
| 2015/0039037 A1 | 2/2015 | Donner et al. | | |
| 2015/0045799 A1 | 2/2015 | Budyansky et al. | | |
| 2019/0110907 A1 * | 4/2019 | Yoko | A61F 2/4684 | |

FOREIGN PATENT DOCUMENTS

| | | |
|---|---|---|
| WO | WO2013179013 A1 | 12/2013 |
| WO | WO2014070804 A1 | 5/2014 |

\* cited by examiner

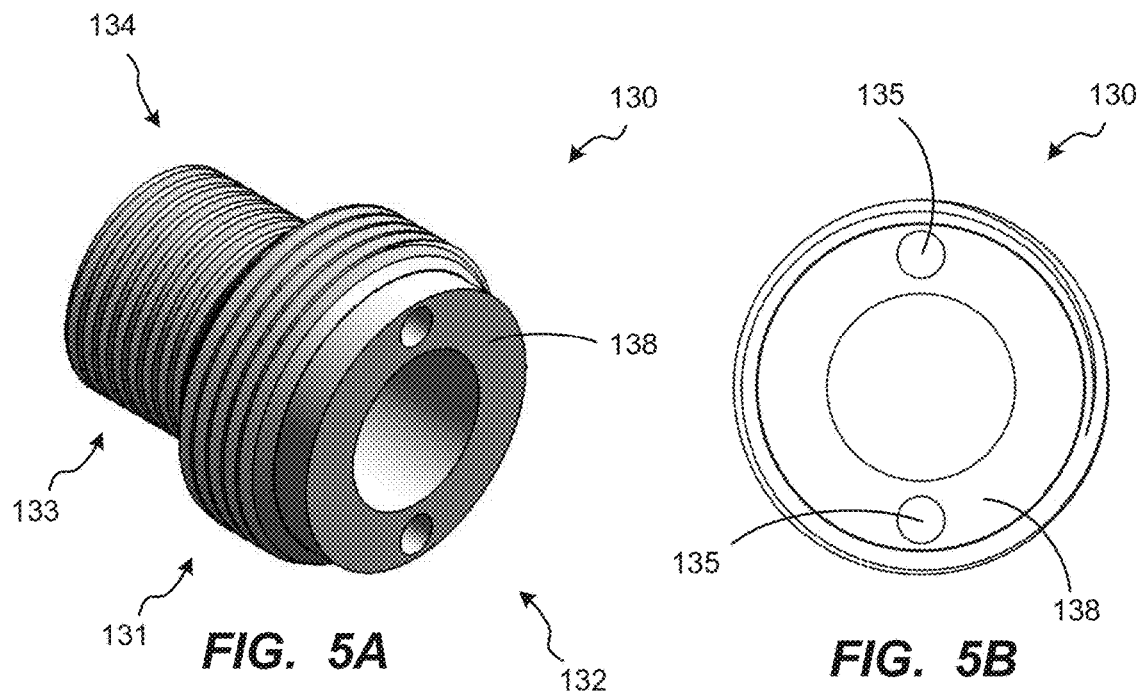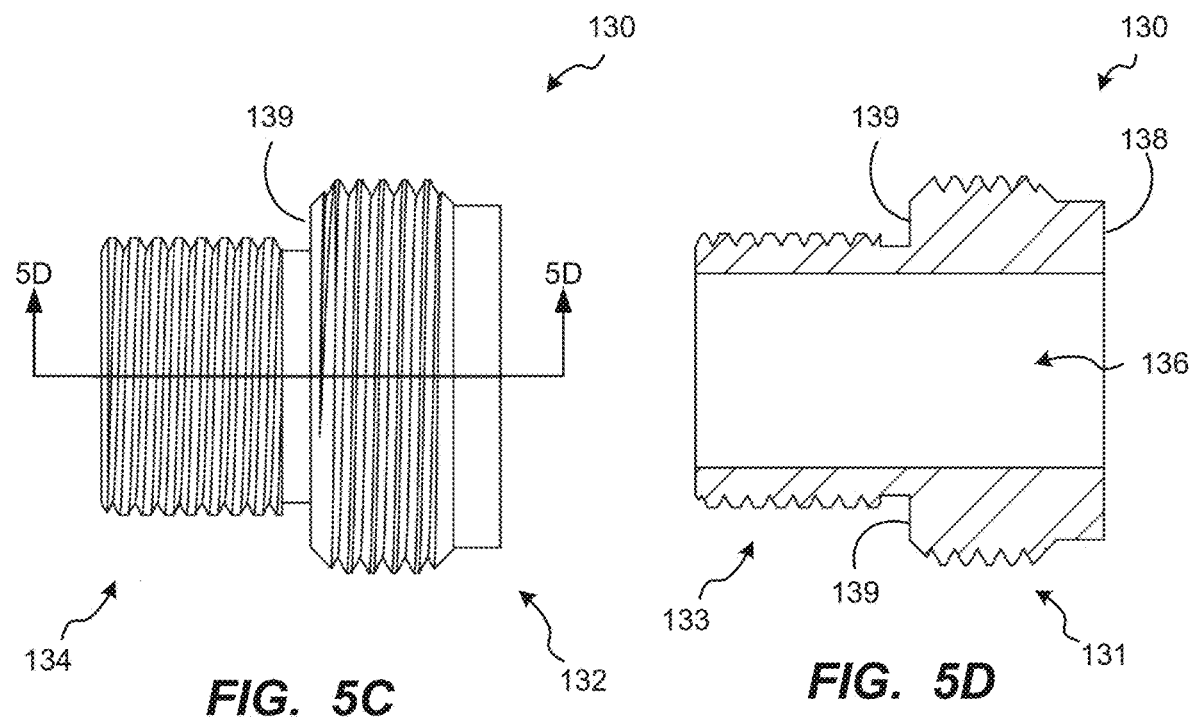

APPARATUS AND METHOD FOR HARVESTING BONE

CROSS-REFERENCE TO RELATED APPLICATIONS

The present application claims the benefit of U.S. Provisional Application Ser. No. 62/199,891, entitled APPARATUS AND METHOD FOR HARVESTING BONE, which was filed on Jul. 31, 2015. The foregoing is incorporated by reference as though set forth herein in its entirety.

TECHNICAL FIELD

The present disclosure relates to surgical instruments and methods. More specifically, the present disclosure relates to a bone harvesting tool with an integrated slap hammer.

BACKGROUND

Frequently, surgeons must harvest bone from the body for diagnostic use, or for therapeutic use such as transplantation to a different part of the body. Many known bone harvesting instruments are unnecessarily cumbersome and/or unwieldy. Once a sample of bone tissue has been captured, the surgeon must often resort to the use of separate tools to withdraw the bone harvesting instrument from the body. Such tools represent a risk of further injury to the patient.

SUMMARY

The various systems and methods of the present disclosure have been developed in response to the present state of the art, and in particular, in response to the problems and needs in the art that have not yet been fully solved by currently available surgical instruments and methods. The systems and methods disclosed herein may provide an enhanced bone harvesting device that provides for easy removal from the bone after a bone sample has been captured.

To achieve the foregoing, and in accordance with the present disclosure, a bone harvesting device may be provided. In one exemplary embodiment, such a device may have a harvester tube, a harvester tube fitting, and a slide hammer. The harvester tube may have a proximal end, a distal end, and a hollow portion intermediate the proximal end and the distal end. The hollow portion may be configured to receive a sample of a bone therein. The harvester tube fitting may be coupled to the proximal end of the harvester tube, and may have a harvester tube fitting impact surface. The slide hammer may be configured to translate along the harvester tube, and may have a slide hammer impact surface positioned to impact the harvest tube fitting impact surface in response to translation of the slide hammer toward the proximal end to urge removal of the proximal end from the bone.

The harvester tube fitting may have a first attachment feature, and the slide hammer may have a second attachment feature configured to detachably couple the slide hammer to the first attachment feature of the harvester tube fitting to selectively prevent the slide hammer from translating along the harvester tube. The first attachment feature and the second attachment feature may have complementary mechanical threading.

The harvester tube fitting impact surface of the harvester tube fitting may define a mechanical stop that prevents the slide hammer from rotating about the harvester tube in a first direction when the slide hammer engages the mechanical stop. The harvester tube fitting and the slide hammer may be configured such that rotating the slide hammer about the harvester tube in a second direction disengages the slide hammer from the mechanical stop. The harvester tube fitting may further have one or more torque features configured to receive a first torque force to facilitate rotation of the slide hammer about the harvester tube in the first direction and a second torque force to facilitate rotation of the slide hammer about the harvester tube in the second direction. The one or more torque features may include two torque apertures formed on a proximally-facing surface of the harvester tube fitting.

The harvester tube fitting may further have a first impact surface and the harvester tube fitting impact surface may be a second impact surface. The first impact surface may be configured to receive an impact force that urges the distal end of the harvester tube into the bone. The device may further include a hammer insert positionable intermediate the slide hammer and the harvester tube fitting. The hammer insert may be configured to receive impact from the slide hammer and transmit the impact to the second impact surface of the harvester tube fitting.

The device may further include a plunger that has a proximal end and a distal end with a point configured to broach cortical bone. The hollow portion of the harvester tube may be configured to slidably receive the plunger therein. The device may further include an end cap coupled to the proximal end of the plunger. The end cap may have a fourth impact surface configured to receive an impact force and transmit the impact force to a proximally-facing surface of the harvester tube fitting. The harvester tube fitting may further have a third attachment feature and the end cap may have a fourth attachment feature configured to detachably couple the plunger to the harvester tube fitting to selectively prevent the plunger from sliding within the hollow portion of the harvester tube.

The slide hammer may have a handle portion with a knurled surface that improves gripping friction. The harvester tube may further have at least one cutting surface positioned at the distal end of the harvester tube. The harvester tube may further have one or more depth gauges that indicate a depth to which the distal end of the harvester tube has been inserted into the bone.

According to one exemplary method, a bone may first be exposed at a harvest site. The bone may include cortical bone and a sample underneath the cortical bone. A bone harvesting device may be positioned above the bone at the harvest site, and may include a harvester tube, a harvester tube fitting, a slide hammer, and a plunger. The harvester tube may have a proximal end, a distal end, and a hollow portion intermediate the proximal end and the distal end. The hollow portion may be configured to receive the sample therein. The harvester tube fitting may be coupled to the proximal end of the harvester tube, and may have a first impact surface, a second impact surface, and a first attachment feature. The slide hammer may be configured to translate along the harvester tube between the proximal end and the distal end of the harvester tube. The plunger may have a proximal end and a distal end with a point configured to broach the cortical bone. The hollow portion of the harvester tube may be configured to slidably receive the plunger therein. The method may further include broaching the cortical bone by driving the distal end of the plunger into the cortical bone, removing the plunger from the harvester tube, driving the distal end of the harvester tube into the bone, capturing the sample inside the hollow portion of the harvester tube, and translating the slide hammer proximally along the harvester tube to impart a force on the harvester tube fitting to urge removal of the harvester tube from the bone.

The harvester tube fitting may have a first attachment feature and the slide hammer may have a second attachment feature. The method may further include, prior to translating the slide hammer proximally along the harvester tube, decoupling the slide hammer from the harvester tube fitting to allow the slide hammer to translate along the harvester tube.

The bone harvesting device may further include an end cap coupled to the proximal end of the plunger. Broaching the cortical bone may include imparting an impact force to an end cap to drive the distal end of the plunger into the cortical bone.

The harvester tube may further have one or more depth gauges. Broaching the cortical bone by driving the distal end of the plunger into the cortical bone may include monitoring a depth of the distal end of the harvester tube within the bone by observing the one or more depth gauges.

Capturing the sample inside the hollow portion of the harvester tube may include rotating the harvester tube in a first direction by rotating the slide hammer in the first direction with a mechanical stop engaged such that rotation of the slide hammer in the first direction causes the harvester tube to rotate in the first direction. Decoupling the slide hammer from the harvester tube fitting may further include rotating the slide hammer in a second direction, opposite to the first direction, about the harvester tube to disengage the mechanical stop, thereby decoupling the slide hammer from the harvester tube fitting. Decoupling the slide hammer from the harvester tube may include applying a torque force to one or more torque features formed in the harvester tube fitting. The one or more torque features may include two torque apertures formed in the first impact surface of the harvester tube fitting.

The method may further include, prior to translating the slide hammer proximally to impart the force on the harvester tube, placing a hammer insert intermediate the slide hammer and the harvester tube fitting. In response to translation of the slide hammer proximally, the force may be transmitted by the slide hammer to the hammer insert and may further be transmitted by the hammer insert to the second impact surface of the harvester tube fitting.

According to one alternative example, such a device may include a plunger, a harvester tube, a harvester tube fitting, and a slide hammer. The plunger may have a proximal end and a distal end with a point configured to broach cortical bone. The harvester tube may have a proximal end, a distal end, and a hollow portion intermediate the proximal end and the distal end. The hollow portion may be configured to slidably receive the plunger therein, and may further be configured to receive a sample of a bone therein. The harvester tube fitting may be coupled to the proximal end of the harvester tube, and may have a first impact surface configured to receive a first impact force that urges the distal end of the harvester tube into the bone, a second impact surface, and a first attachment feature. The slide hammer may be configured to translate along the harvester tube, and may include a slide hammer impact surface positioned to impact the second impact surface in response to translation of the slide hammer toward the proximal end to urge removal of the proximal end from the bone, and a second attachment feature configured to detachably couple the slide hammer to the first attachment feature of the harvester tube fitting to selectively prevent the slide hammer from translating along the harvester tube.

These and other features and advantages of the present disclosure will become more fully apparent from the following description and appended claims, or may be learned by the practice of the systems and methods set forth hereinafter.

BRIEF DESCRIPTION OF THE DRAWINGS

Exemplary embodiments will become more fully apparent from the following description and appended claims, taken in conjunction with the accompanying drawings. Understanding that these drawings depict only exemplary embodiments and are, therefore, not to be considered limiting of the appended claims, exemplary embodiments will be described with additional specificity and detail through use of the accompanying drawings in which:

FIG. 5A is an isometric view of the harvester tube fitting of FIG. 1 viewed from the proximal end of the harvester tube fitting.

FIG. 5B is a front view of the proximal end of the harvester tube fitting of FIG. 1.

FIG. 5C is a side view of the harvester tube fitting of FIG. 1.

FIG. 5D is a cross-sectional side view of the harvester tube fitting of FIG. 5C, taken along the section line 5D-5D of FIG. 5C.

DETAILED DESCRIPTION

Exemplary embodiments will be best understood by reference to the drawings, wherein like parts are designated by like numerals throughout. It will be readily understood that the components described and illustrated in the Figures herein could be arranged and designed in a wide variety of different configurations. Thus, the following more detailed description of the embodiments of the apparatus and method, as represented in FIGS. 1 through 8, is not intended to limit the scope of the appended claims or those of any other application claiming priority to this application, but is merely representative of exemplary embodiments.

The phrases "connected to," "coupled to," and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Some surgical procedures include harvesting bone, bone marrow, bone cells, or other soft bony tissue for placement in other parts of the body to culture bone fusion or bone formation. Such procedures may include, but are not limited to: orthopedic, neurosurgical, spinal, ear-nose-throat, oral maxillofacial, rheumatology procedures, or the like. Bone harvesting often includes a surgical procedure involving exposure of a suitable bone harvest site, such as the iliac crest, ulna, radius, femur, or the like. The bone harvest site may be exposed with a small incision over the donor site to expose the bone. The bone may then be harvested by driving an appropriate coring device into the bone. However, it may be difficult to remove the coring device from the bone once the coring device has been driven into the bone. Thus, quick, effective, and/or low cost systems and methods for removing bone harvesting devices from the bone after they have been driven into the bone may be desirable.

Figure 1:
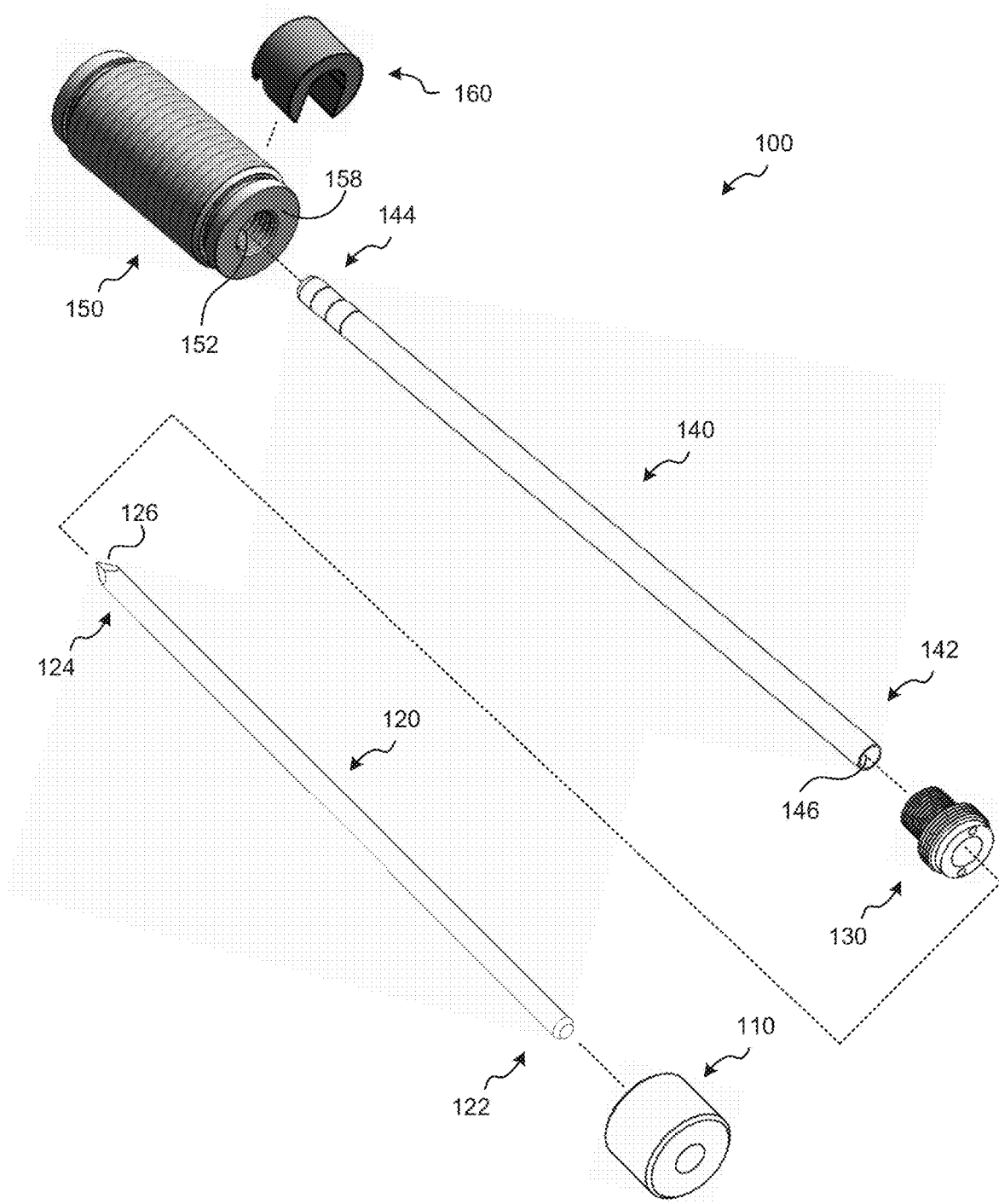
FIG. 1 is an exploded view of a bone harvesting device, according to one embodiment.

FIG. 1 is an exploded view of a bone harvesting device 100, according to one embodiment. The bone harvesting device 100 may facilitate the process of harvesting bone from a donor site (not shown), and may more specifically facilitate removal of the bone harvesting device 100 from the bone after the bone harvesting device 100 has been driven into the bone. The bone harvesting device 100 shown in FIG. 1 may include an end cap 110, a plunger 120, a harvester tube fitting 130, a harvester tube 140, a slide hammer 150, and a hammer insert 160. Each individual part of the bone harvesting device 100 will be described in more detail with reference to FIGS. 3A-7D.

Continuing with FIG. 1, the plunger 120 may have a proximal end 122 and a distal end 124. Likewise, the harvester tube 140 may have a proximal end 142 and a distal end 144. The end cap 110 may be coupled to the proximal end 122 of the plunger 120 to form a plunger assembly 400 (see FIG. 4B). Likewise, the harvester tube fitting 130 may be coupled to the proximal end 142 of the harvester tube 140 to form a harvester tube assembly 600 (see FIG. 6C). The harvester tube 140 may be cylindrical in shape and may include a hollow portion 146 that forms a channel intermediate the proximal end 142 and the distal end 144 of the harvester tube 140. The hollow portion 146 may span the length of the harvester tube 140 (see FIG. 6B). The hollow portion 146 may be configured to slidably receive the plunger 120 therein by inserting the distal end 124 of the plunger 120 into the proximal end 142 of the harvester tube 140.

The distal end 124 of the plunger 120 may form a point 126 configured to broach hard cortical bone. The point 126 of the plunger 120 may protrude from the distal end 144 of the harvester tube 140 when the plunger 120 is fully inserted into the harvester tube 140. In at least one embodiment, the plunger 120 may be secured inside the hollow portion 146 of the harvester tube 140 by one or more complementary attachment features associated with the end cap 110 and the harvester tube fitting 130, as will be discussed in more detail below.

The slide hammer 150 may have an aperture 156 that is greater in diameter than the diameter of the harvester tube 140 such that the harvester tube 140 may be received inside the aperture 156. The slide hammer 150 may freely translate along the harvester tube 140 between the proximal end 142 and the distal end 144 of the harvester tube 140. The slide hammer 150 and the harvester tube fitting 130 may include one or more complementary attachment features configured to detachably couple the slide hammer 150 to the harvester tube fitting 130, as will be discussed in more detail below. In this manner, a user (not shown) may prevent the slide hammer 150 from translating along the harvester tube 140 by engaging the one or more complementary attachment features.

The hammer insert 160 may be used during the process of removing the harvester tube 140 from the bone after the harvester tube 140 has been driven into the bone. This process will also be discussed in more detail below. The hammer insert 160 may be configured to detachably couple to the slide hammer 150 and the end cap 110, as shown in FIGS. 2A-2C.

Any part or portion of the bone harvesting device 100 shown in FIG. 1 may be made of any suitable material, including but not limited to: any type of metal, metal alloy, plastic, rubber, silicone, or any other material suitable for use in a medical device. In some embodiments, metals such as stainless steel and Titanium may beneficially be used.

Figure 2A:
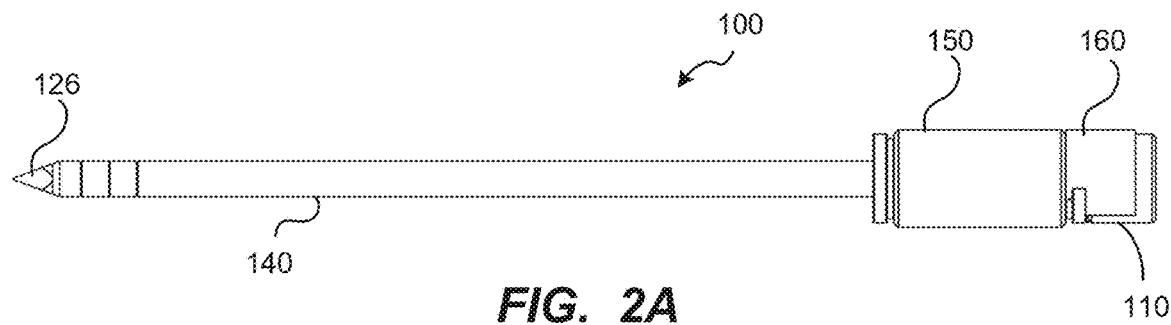
FIG. 2A is a side view of the bone harvesting device of FIG. 1.
Figure 2B:
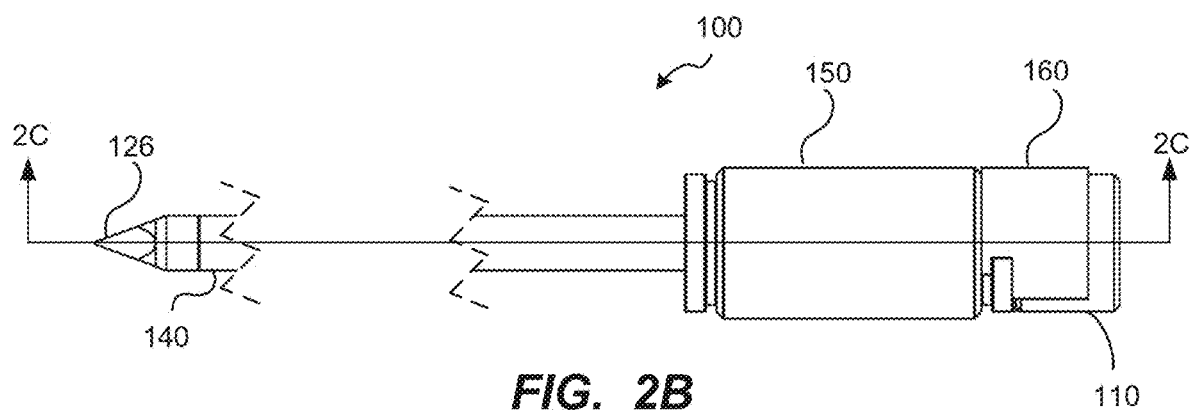
FIG. 2B is an enlarged, broken side view of the bone harvesting device of FIG. 2A.
Figure 2C:
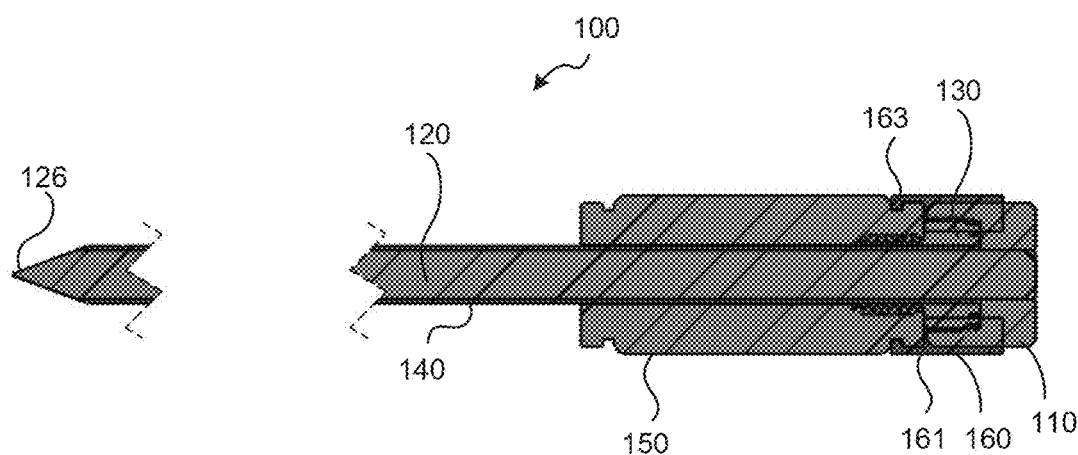
FIG. 2C is a cross-sectional side view of the assembled bone harvesting device of FIG. 2B, taken along the section line 2C-2C of FIG. 2B.

FIGS. 2A through 2C are various side views of the bone harvesting device 100 of FIG. 1 in assembled form. Specifically, FIG. 2A is a side view of the bone harvesting device 100. FIG. 2B is an enlarged, broken side view of the bone harvesting device 100 of FIG. 2A having a section line 2C-2C. FIG. 2C is a cross-sectional side view of the assembled bone harvesting device 100 of FIG. 2B, taken along the section line 2C-2C of FIG. 2B.

FIGS. 2A through 2C depict the bone harvesting device 100 in a fully assembled condition, ready for use to penetrate bone tissue. The end cap 110 is coupled to the proximal end 122 of the plunger 120, the harvester tube fitting 130 is coupled to the proximal end 142 of the harvester tube 140, the end cap 110 is fastened to the proximal end 132 of the harvester tube fitting 130, the proximal end 152 of the slide hammer 150 is fastened to the distal end 134 of the harvester tube fitting 130, and the hammer insert 160 is clipped over the slide hammer 150 and the end cap 110. In the assembled state shown in FIGS. 2A-2C, the slide hammer 150 is not free to translate along the harvester tube 140 and the plunger 120 is secured in place inside the harvester tube 140 with the point 126 of the plunger 120 protruding from the distal end 144 of the harvester tube 140.

Figure 3A:
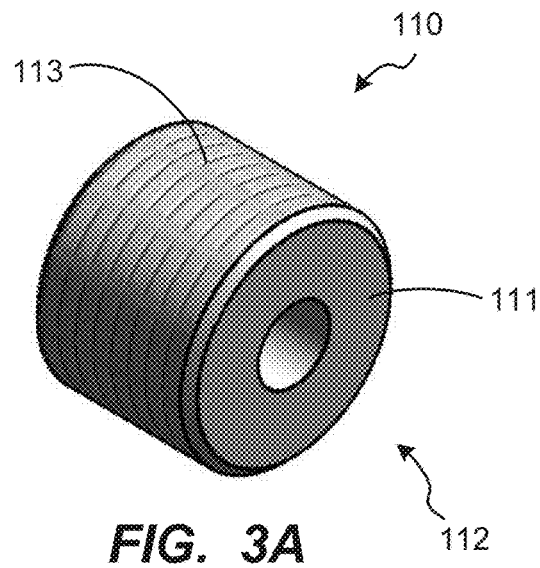
FIG. 3A is an isometric view of the end cap of FIG. 1 as viewed from a proximal end of the end cap.
Figure 3B:
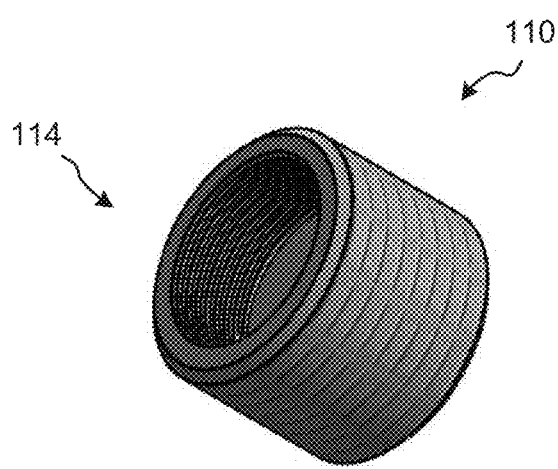
FIG. 3B is another isometric view of the end cap of FIG. 1 as viewed from a distal end of the end cap.
Figure 3C:
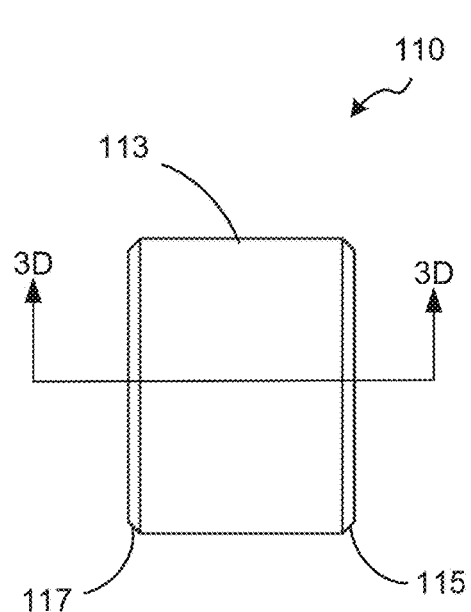
FIG. 3C is a side view of the end cap of FIG. 1.
Figure 3D:
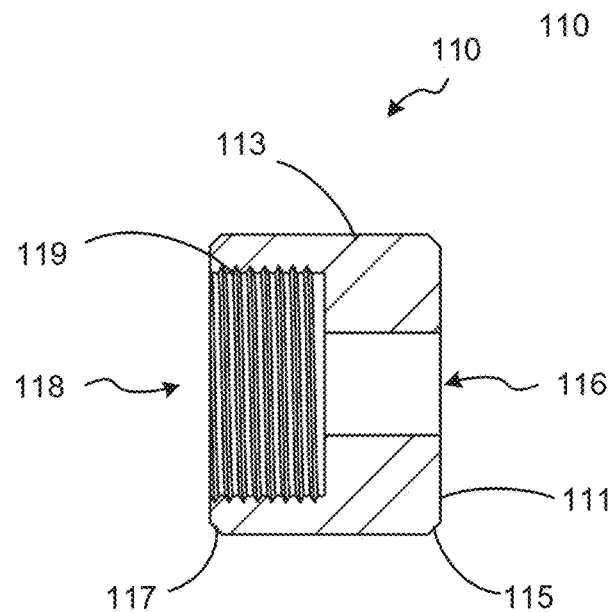
FIG. 3D is a cross-sectional side view of the end cap of FIG. 3C, taken along the section line 3D-3D of FIG. 3C.

FIGS. 3A through 3D illustrate various views of the end cap 110 of FIG. 1. Specifically, FIG. 3A is an isometric view of the end cap 110 as viewed from a proximal end 112 of the end cap 110. FIG. 3B is another isometric view of the end cap 110 as viewed from a distal end 114 of the end cap 110. FIG. 3C is a side view of the end cap 110 having a section line 3D-3D. FIG. 3D is a cross-sectional side view of the end cap 110 of FIG. 3C, taken along the section line 3D-3D of FIG. 3C.

The end cap 110 may be generally cylindrical in shape and may include a first aperture 116 with a first diameter and a second aperture 118 with a second diameter. The first aperture 116 may be configured to receive and couple to the proximal end 122 of the plunger 120. In some embodiments, the first aperture 116 may be permanently secured to the proximal end 112 of the plunger 120 to secure the plunger 120 to the end cap 110, as will be described below.

The second aperture 118 may include a fourth attachment feature 119, which will be explained below in greater detail with reference to a complementary attachment feature associated with the harvester tube fitting 130. In at least one embodiment, the fourth attachment feature 119 may include mechanical threading configured to receive complementary mechanical threads formed on the harvester tube fitting 130 and configured to detachably couple the plunger 120 to the harvester tube fitting 130 to selectively prevent the plunger 120 from sliding within the hollow portion 146 of the harvester tube 140. However, it will be understood that any suitable attachment feature may be used.

The proximal end 112 of the end cap 110 may define a fourth impact surface 111 configured to receive in impact force from a suitable tool, such as a mallet (not shown). The outer surface 113 of the end cap 110 may be gripped by the user and rotated to selectively couple the end cap 110 to the harvester tube fitting 130. The outer surface 113 may be knurled, ridged, and/or coated with a different material such as a plastic or rubber material to increase gripping friction. The end cap 110 may also include chamfered edges 115, 117 on the proximal end 112 and the distal end 114 of the end cap 110.

Figure 4A:
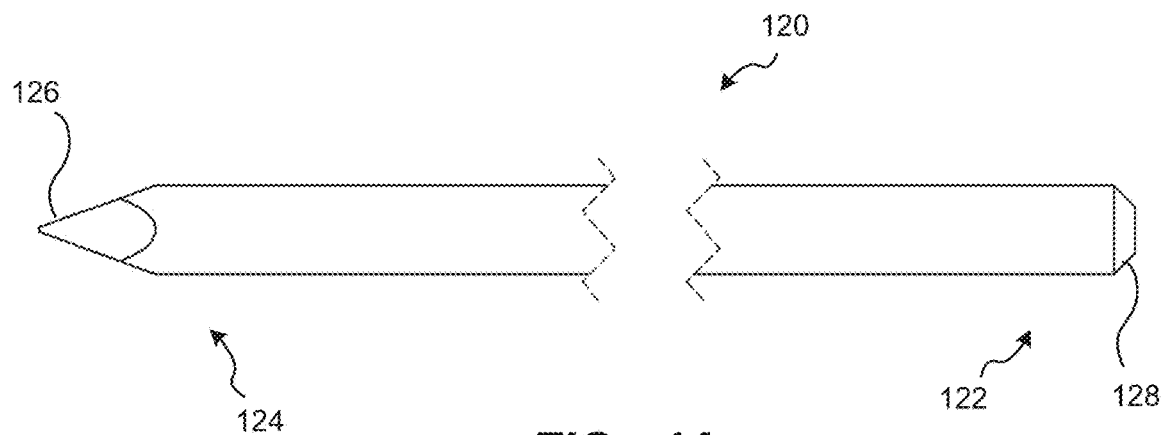
FIG. 4A is a side view of the plunger of FIG. 1.

FIG. 4A is a side view of the plunger 120 shown in FIG. 1. The plunger 120 may be generally cylindrical in shape. In at least one embodiment, the proximal end 122 of the plunger 120 may include a weld chamfer 128, which may be used to facilitate coupling of the end cap 110 to the proximal end 122 of the plunger 120. The point 126 formed on the distal end 124 of the plunger 120 may be made by any number of converging sides including, but not limited to a three-sided point or a four-sided point. Alternatively, the point 126 may be formed by one continuous cone-shaped surface terminating in the point 126. The point 126 may be sharp, or may have a small flat, rounded, or otherwise curved surface. The plunger 120 may be made of any material with sufficient strength and rigidity to broach cortical bone or other bony tissue.

Figure 4B:
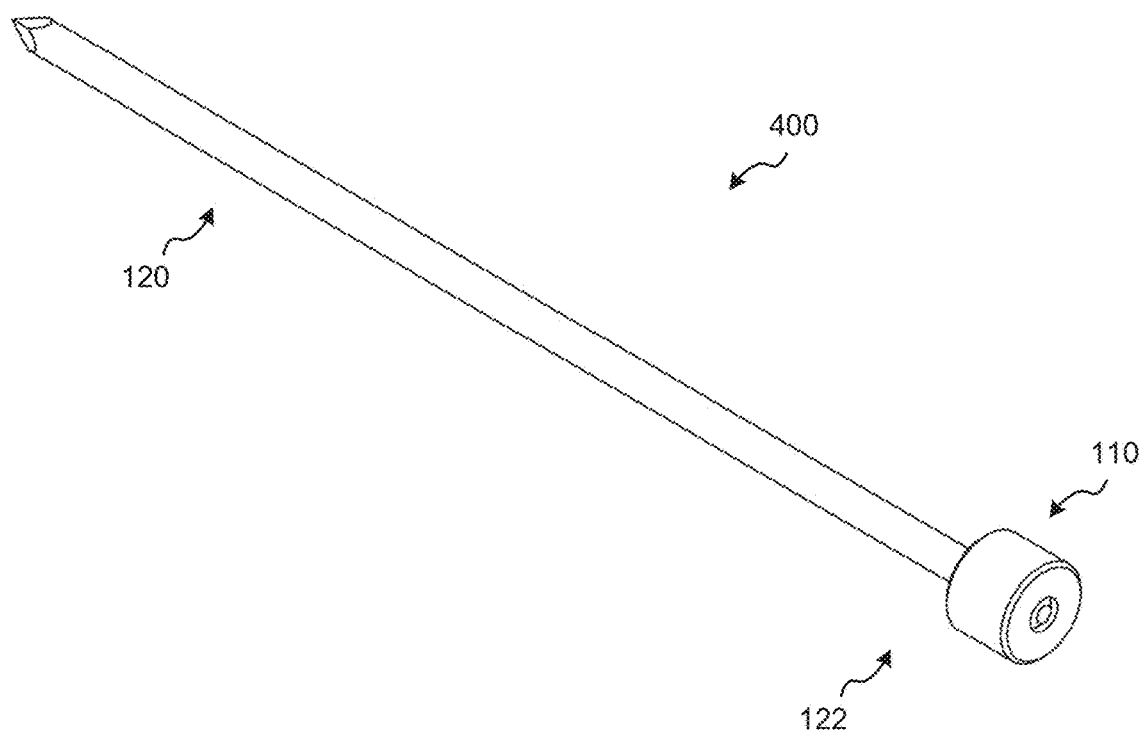
FIG. 4B is an isometric view of the plunger assembly of FIG. 1.

FIG. 4B is an isometric view of the plunger assembly 400. The plunger assembly 400 may include the end cap 110 and plunger 120 of FIG. 1 coupled together, according to at least one embodiment. The end cap 110 may be coupled to the proximal end 122 of the plunger 120 by any suitable method including, but not limited to: welding, compression fitting, adhesive, integral formation, and the like.

FIGS. 5A through 5D are various views of the harvester tube fitting 130 of FIG. 1. Specifically, FIG. 5A is an isometric view of the harvester tube fitting 130 viewed from the proximal end 132 of the harvester tube fitting 130. FIG. 5B is a front view of the proximal end 132 of the harvester tube fitting 130. FIG. 5C is a side view of the harvester tube fitting 130 having a section line 5D-5D. FIG. 5D is a cross-sectional side view of the harvester tube fitting 130 of FIG. 5C, taken along the section line 5D-5D of FIG. 5C.

The harvester tube fitting 130 may be generally cylindrical in shape with the proximal end 132 of the harvester tube fitting 130 having a larger outer diameter than the distal end 134 of the harvester tube fitting 130. The harvester tube fitting 130 may have an aperture 136 formed therethrough and configured to receive the proximal end 142 of the harvester tube 140. The harvester tube fitting 130 may be coupled to the proximal end 142 of the harvester tube 140 by any suitable method including, but not limited to: welding, compression fitting, adhesive, integral formation, and the like. The harvest tube fitting 130 may optionally be permanently secured to the harvester tube 140.

The proximal end 132 of the harvester tube fitting 130 may include a first impact surface 138 configured to receive a first impact force to drive the harvester tube 140 into the bone. The harvester tube fitting 130 may also include a second impact surface 139 intermediate the proximal end 132 and the distal end 134 of the harvester tube fitting 130. The second impact surface 139 may be configured to receive a second impact force from the slide hammer 150 to facilitate removal of the harvester tube 140 from bone.

The proximal end 132 of the harvester tube fitting 130 may include a first attachment feature 131 and the distal end 134 of the harvester tube fitting 130 may include a third attachment feature 133. In at least one embodiment, the first attachment feature 131 and the third attachment feature 133 may include mechanical threading configured to interact with complementary mechanical threading formed in the slide hammer 150 and end cap 110 respectively. However, it will be understood that any suitable attachment feature style may be used without departing from the spirit or scope of the present disclosure. For example, in alternative embodiments (not shown), various bayonet fittings, clips, clasps, and/or the like may be used.

In at least one embodiment, the second impact surface 139 may also act as a mechanical stop for the slide hammer 150. For example, the slide hammer 150 may be threaded onto the harvester tube fitting 130 by rotating the slide hammer 150 in a first direction causing the slide hammer 150 to translate in the proximal direction. However, with enough translation in the proximal direction a third impact surface 158 of the slide hammer 150 will eventually come into contact with the second impact surface 139 of the harvester tube fitting 130 and the slide hammer 150 will be prevented from any further rotation in the first direction or any further translation in the proximal direction. In this state, the mechanical stop is engaged and any further rotation of the slide hammer in the first direction will also cause the harvester tube 140 to rotate in the first direction. In this manner, the mechanical stop formed by the second impact surface 139 may help facilitate the capture of soft bony tissue inside the hollow portion 146 of the harvester tube 140 by allowing the user to easily rotate the harvester tube 140 to cut or shear off pieces of soft bony tissue.

Once the harvester tube 140 has been inserted into the bone and soft bony tissue has been captured in the hollow portion 146 of the harvester tube 140, the harvester tube 140 may be extracted from the bone to harvest the soft bony tissue. To accomplish this, the mechanical stop may be disengaged by rotating the slide hammer 150 in a second direction relative to the harvester tube 140 and the slide hammer may be decoupled from the harvest tube fitting 130. However, friction between the second impact surface 139 and the third impact surface 158 may resist efforts to disengage the mechanical stop. Accordingly, one or more torque features may be formed in the harvester tube fitting 130 to help overcome these frictional forces, as well as facilitate coupling and decoupling of the slide hammer 150 to the harvester tube fitting 130.

In at least one embodiment, the one or more torque features may include two torque apertures 135 formed in the first impact surface 138 of the harvester tube fitting 130. However, it will be understood that any suitable torque feature shape or style may be used without departing from the spirit or scope of the present disclosure. The two torque apertures 135 may be configured to receive an appropriate torque tool (not shown) to enable the user to hold the harvester tube fitting 130 steady while applying a rotational force to the slide hammer 150 in the second direction to overcome the frictional forces of the mechanical stop to disengage the mechanical stop. Thus, in general, the one or more torque features may be configured to receive a first torque force to facilitate rotation of the slide hammer 150 about the harvester tube 140 in the first direction and a second torque force to facilitate rotation of the slide hammer 150 about the harvester tube 140 in the second direction.

Figure 6A:
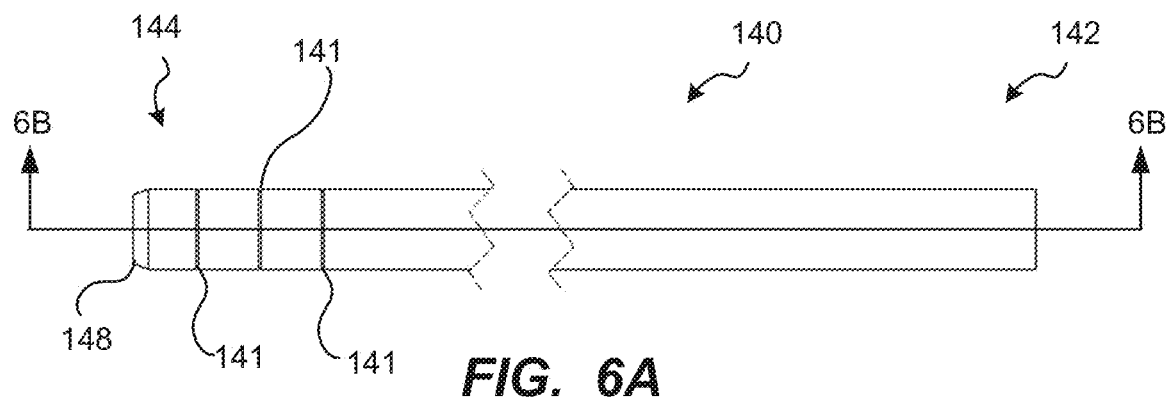
FIG. 6A is a side view of the harvester tube of FIG. 1.
Figure 6B:
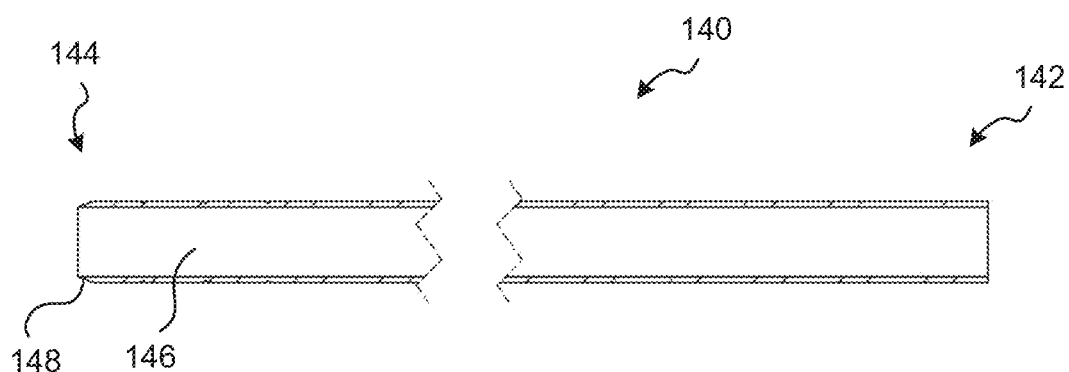
FIG. 6B is a cross-sectional side view of the harvester tube of FIG. 6A, taken along the section line 6B-6B in FIG. 6A.

FIG. 6A is a side view of the harvester tube 140 of FIG. 1 with a section line 6B-6B. FIG. 6B is a cross-sectional side view of the harvester tube 140 of FIG. 6A, taken along the section line 6B-6B in FIG. 6A. In at least one embodiment, the harvester tube 140 may be generally tubular in shape with the hollow portion 146 of the harvester tube 140 forming a channel extending through the harvester tube 140. The distal end 144 of the harvester tube 140 may include at least one cutting surface 148. In at least one embodiment, the at least one cutting surface 148 may include a chamfer that causes the cutting surface to taper to a sharp edge with a circular shape. However, it will be understood that any suitable cutting surface style or shape may be used without departing from the spirit or scope of the present disclosure, such as serrated edges and the like. The at least one cutting surface 148 may be made of any suitable material that may be used to cut through bone.

The distal end 144 of the harvester tube 140 may also include one or more markings, or depth gauges 141, to help the user monitor how deep the distal end 144 of the harvester tube 140 is being driven into the bone. The one or more depth gauges 141 may be formed by any suitable technique. For example, the one or more depth gauges 141 may be formed by laser etching. In at least one embodiment, the one or more depth gauges 141 include three depth gauges spaced apart from each other (and the at least one cutting surface 148) in about 1 cm increments. If desired, indicia may also be marked, etched, or otherwise provided on the exterior surface of the harvester tube 140, proximate the depth gauges 141, to indicate the depth for each of the depth gauges 141.

Figure 6C:
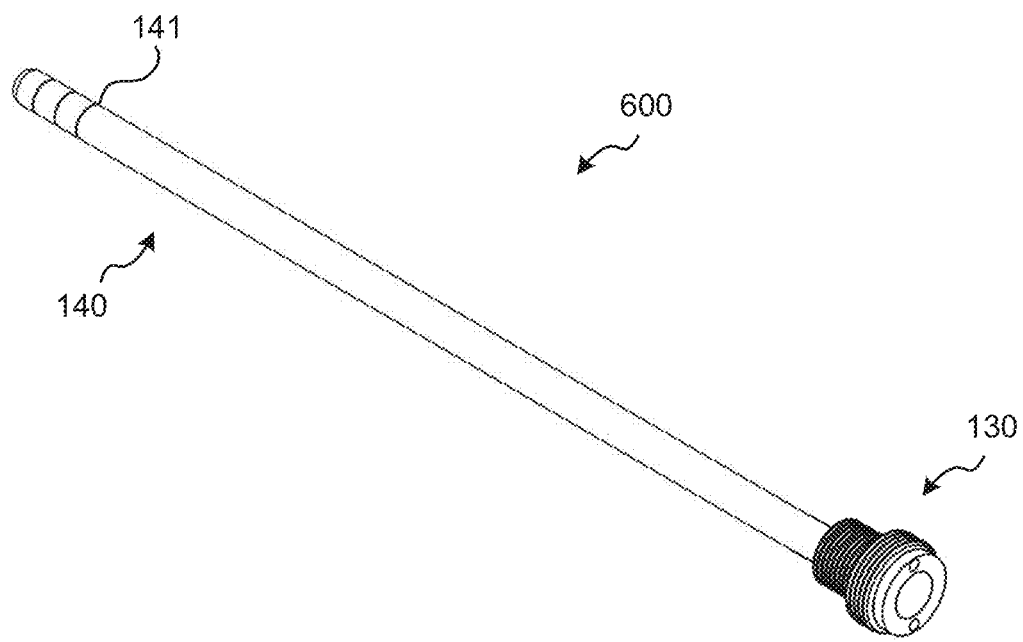
FIG. 6C is an isometric view of the harvester tube assembly of FIG. 1.

FIG. 6C is an isometric view of a harvester tube assembly 600 according to FIG. 1. The harvester tube assembly 600 may include the harvester tube fitting 130 and the harvester tube 140 of FIG. 1 coupled together, according to at least one embodiment. The harvester tube fitting 130 may be coupled to the proximal end 142 of the harvester tube 140 by any suitable method including, but not limited to: welding, compression fitting, adhesive, integral formation, and the like. As mentioned previously, this attachment may optionally be permanent.

Figure 7A:
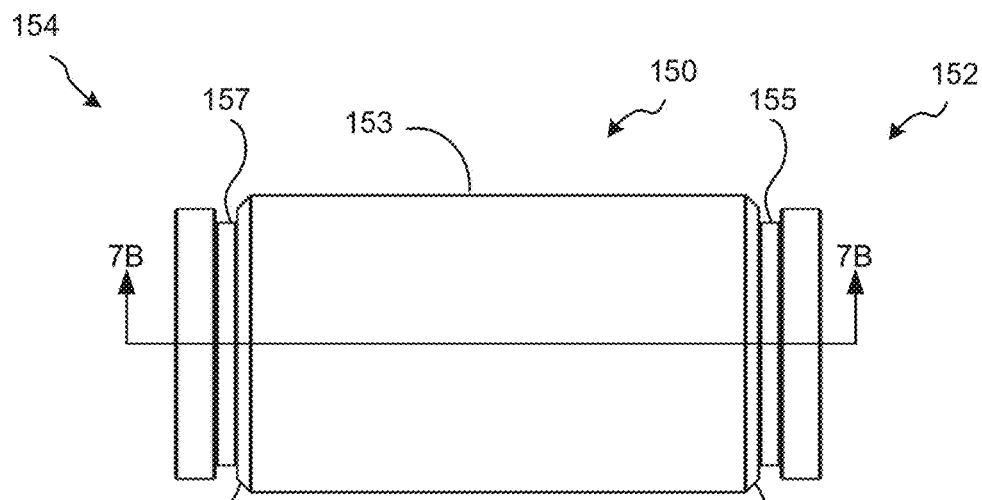
FIG. 7A is a side view of the slide hammer of FIG. 1.
Figure 7B:
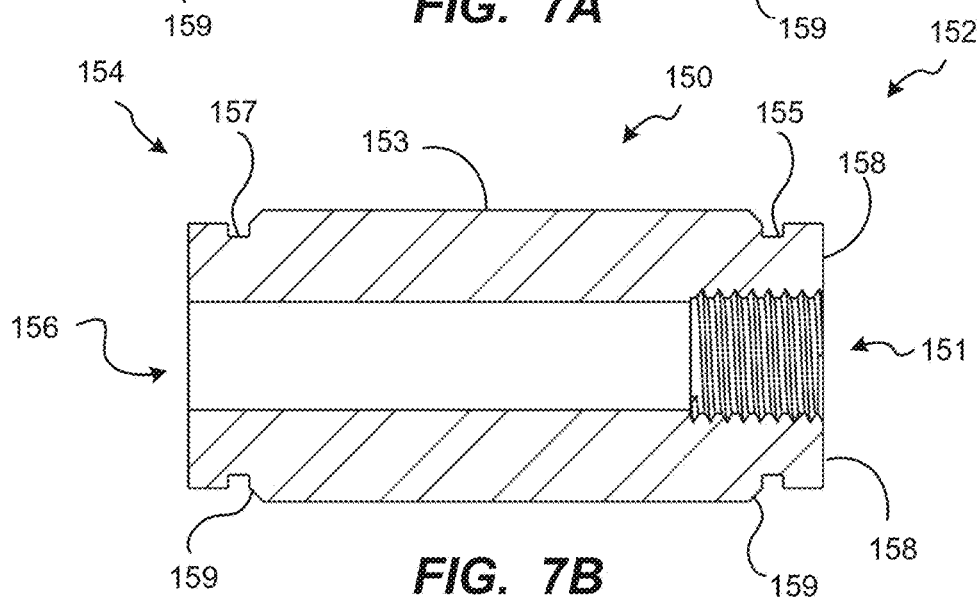
FIG. 7B is a cross-sectional side view of the slide hammer of FIG. 7A, taken along the section line 7B-7B in FIG. 7A.

FIG. 7A is a side view of the slide hammer 150 of FIG. 1 with a section line 7B-7B. FIG. 7B is a cross-sectional side view of the slide hammer 150 of FIG. 7A, taken along the section line 7B-7B in FIG. 7A.

The slide hammer 150 may be generally cylindrical in shape with a proximal end 152, a distal end 154, and an aperture 156 formed about a central axis of the slide hammer 150. The aperture 156 may have a larger diameter than the harvester tube 140 such that the harvester tube 140 may be slidably received inside the aperture 156. Thus, the slide hammer 150 may translate along the harvester tube 140 between the proximal end 142 and the distal end 144 of the harvester tube 140.

The slide hammer 150 may include a second attachment feature 151 at the proximal end 152 of the slide hammer 150. The second attachment feature 151 may be configured to detachably couple the slide hammer 150 to the third attachment feature 133 of the harvester tube fitting 130 to selectively prevent the slide hammer 150 from translating along the harvester tube 140. In at least one embodiment, the second attachment feature 151 may include mechanical threading configured to selectively couple with complementary mechanical threading formed in the harvester tube fitting 130. However, it will be understood that any suitable attachment feature or style may be used without departing from the spirit or scope of the present disclosure. In alternative embodiments (not shown), various bayonet fittings, clips, clasps, and/or other attachment features may be used.

The proximal end 152 of the slide hammer 150 may include a third impact surface 158 configured to impart a force to the second impact surface 139 either directly or indirectly as will be explained below with reference to FIGS. 7C and 7D. The slide hammer 150 may also include an integrated handle portion 153 to facilitate gripping the slide hammer 150. The handle portion 153 may be intermediate a first depression 155 and a second depression 157 formed in the slide hammer 150. The handle portion 153 may also include chamfered surfaces 159 adjacent the first depression 155 and the second depression 157. The surface of the handle portion 153 may have patterns formed therein to increase gripping friction, such as a knurled surface, or any other suitable pattern. The handle portion 153 may be made from or coated with a different material than the rest of the slide hammer 150 to increase gripping friction. Such materials may include, but are not limited to, plastic, rubber, silicone, combinations thereof.

Figures 7C, 7D:
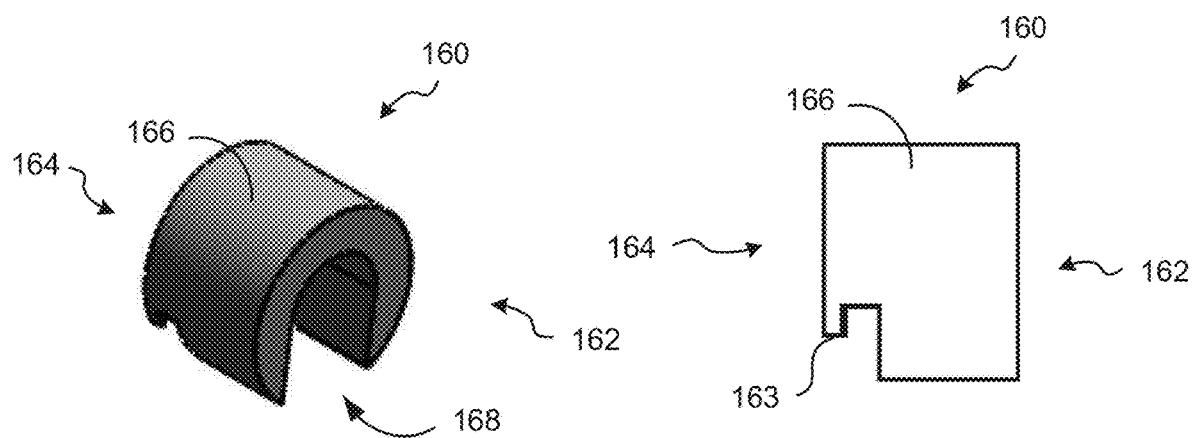
FIG. 7C is an isometric view of the hammer insert of FIG. 1.
FIG. 7D is a side view of the hammer insert of FIG. 7C.

FIG. 7C is an isometric view of the hammer insert 160 of FIG. 1 and FIG. 7D is a side view of the hammer insert 160 of FIG. 7C. The hammer insert 160 may be coupled to and/or stored on the bone harvesting device 100, as shown in FIGS. 2A-2C. The hammer insert 160 may be generally cylindrical in shape with a proximal end 162, a distal end 164, an outer surface 166, an opening 168, a first lip 161, and a second lip 163 (see FIG. 2C). The opening 168 may form an interior space configured to receive portions of the slide hammer 150 and the end cap 110.

The opening 168, first lip 161, and second lip 163 may be configured to removably couple the hammer insert 160 to the slide hammer 150 and the end cap 110 as shown in FIGS. 1 through 2C. Specifically, when the bone harvesting device 100 is fully assembled as in FIGS. 2A through 2C, the second lip 163 may engage the first depression 155 of the slide hammer 150, and the first lip 161 may reside between the third impact surface 158 and the distal end of the end cap 110.

The proximal end 162 of the hammer insert 160 may optionally be positioned between the fourth impact surface 111 and the distal end of the end cap 110, as shown in FIGS. 2A through 2C. The proximal end 162 of the hammer insert 160 optionally be received in a groove (not shown) encircling the exterior surface of the end cap 110. In alternative embodiments, the hammer insert 160 may be sufficiently long to enable the proximal end 162 of the hammer insert 160 to be positioned proximal to the fourth impact surface 111 of the end cap 110 when the bone harvesting device 100 is fully assembled. In either case, the hammer insert 160 may help to keep the bone harvesting device 100 in the fully assembled state until the user removes the hammer insert 160 to permit the slide hammer 150 to be unscrewed from the harvest tube fitting 130.

In at least one embodiment, the hammer insert 160 may be placed intermediate the slide hammer 150 and the harvester tube fitting 130. In this manner, the hammer insert 160 may receive a second impact force from the slide hammer 150 and transmit the second impact force to the second impact surface 139 of the harvester tube fitting 130. In one embodiment, the user may translate the slide hammer 150 toward the hammer insert 160, striking the distal end 164 of the hammer insert 160 with the proximal end 152 (or the third impact surface 158) of the slide hammer 150. The second impact force may be transmitted through the hammer insert 160 to the proximal end 162 of the hammer insert 160, then transmitted to the second impact surface 139 of the harvester tube fitting 130.

In one alternative embodiment, the hammer insert 160 may be removed to permit the slide hammer 150 to be decoupled from the harvest tube fitting 130 and moved distally away from the harvest tube fitting 130. The hammer insert 160 may then be reattached to the proximal end 152 of the slide hammer 150 as depicted in FIGS. 2A through 2C, and the slide hammer 150 may slide proximally along the harvester tube 140 and may carry the hammer insert 160 with it such that the proximal end 162 of the hammer insert 160 strikes the second impact surface 139 of the harvest tube fitting 130.

Figure 8:
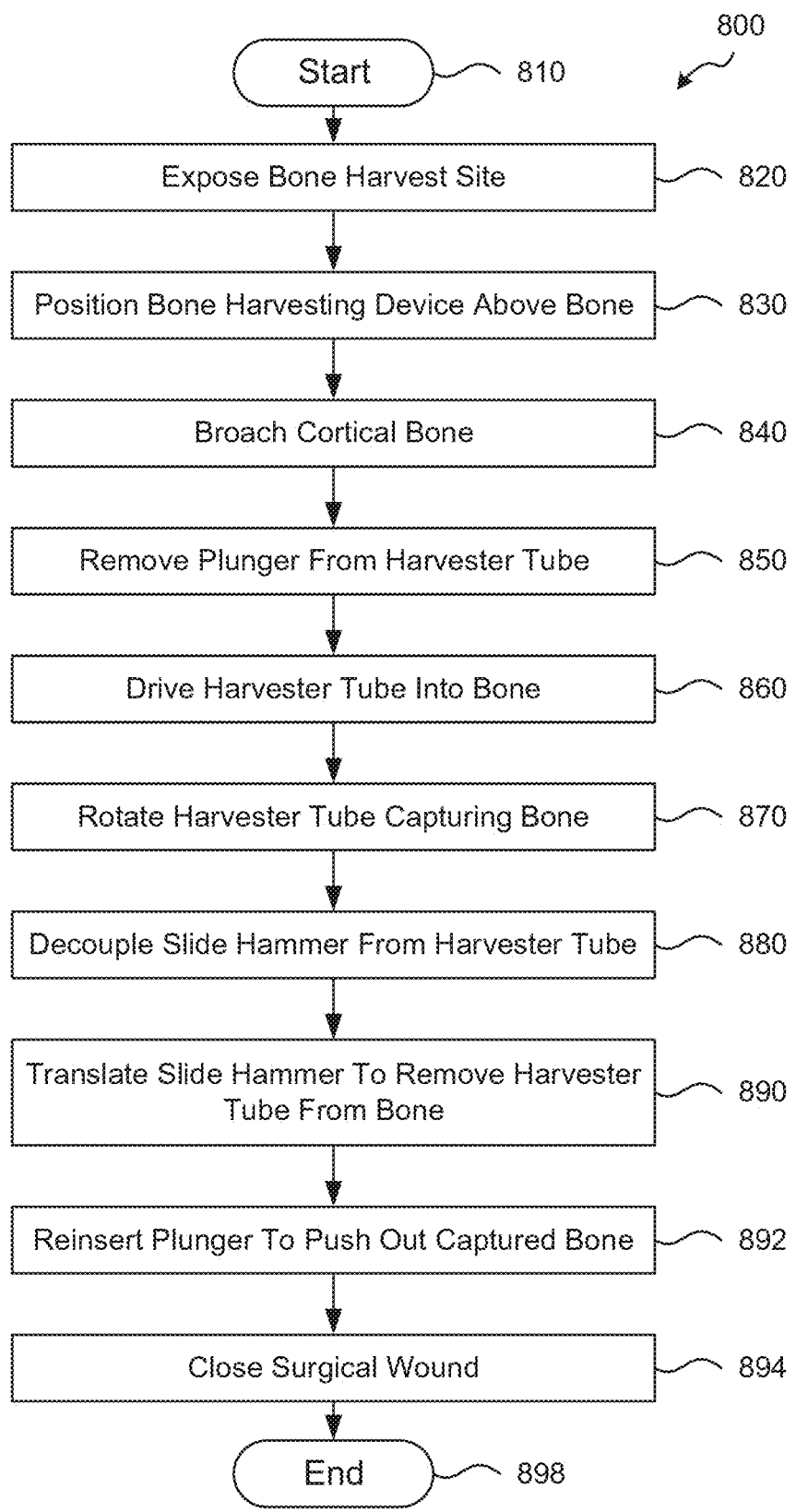
FIG. 8 is a flowchart of a method by which the bone harvesting device may be used to harvest bone.

FIG. 8 is a flowchart of a method 800 by which the bone harvesting device 100 may be used to harvest bone. FIG. 8 is merely exemplary; a bone harvesting device according to the present disclosure may be used in conjunction with other methods. Further, the method 800 of FIG. 8 may be carried out through the use of bone harvesting devices different from the bone harvesting device 100 of FIG. 1.

The method 800 may start 810 with a step 820 in which a bone harvest site (not shown) is exposed to provide access to bone for harvesting. This may be accomplished via methods known in the art. For example, if the iliac crest is chosen as the bone harvesting site, a small incision or surgical wound may be created above the iliac crest and a wide variety of retractors known in the art may then be used to maintain exposure of the bone harvest site during surgery.

Once the proper access has been obtained, the method 800 may proceed to a step 830 in which the bone harvesting device 100 may be positioned above the bone at the harvest site. The bone harvesting device 100 may be positioned to abut, or otherwise be brought into contact with, the bone that is to be harvested.

After the bone harvesting device 100 has been positioned, the method 800 may proceed to a step 840 in which the user may proceed to broach any hard cortical bone that may be present at the bone harvest site by driving the distal end 124 of the plunger 120 into the cortical bone to broach the cortical bone. This may be accomplished by using a mallet (not shown) to impart an impact force to the fourth impact surface 111 on the proximal end 112 of the end cap 110 to drive the point 126 formed on the distal end 124 of the plunger 120 into the cortical bone.

Once any cortical bone has been broached by the plunger 120, the method 800 may proceed to a step 850 in which the plunger assembly 400 may be removed from the harvester tube 140. This may be accomplished by rotating the end cap 110 to decouple the end cap 110 from the harvester tube fitting 130 and then withdrawing the plunger assembly 400 proximally, causing the plunger 120 to pass out of the proximal end 142 of the harvester tube 140.

After the plunger assembly 400 has been removed from the harvester tube 140, the method 800 may proceed to a step 860 in which the distal end 144 of the harvester tube 140 may be driven into the soft bony tissue. This may be accomplished by using a mallet to impart an impact force to the first impact surface 138 on the proximal end 132 of the harvester tube fitting 130 that is coupled to the harvester tube 140. Monitoring the depth of the distal end 144 of the harvester tube 140 in the bone may also be accomplished by observing the one or more depth gauges 141 visibly marked on the harvester tube 140, as previously discussed.

Once the harvester tube 140 has been driven into the soft bony tissue to the desired depth, the method 800 may proceed to a step 870 in which the soft bony tissue may be cut, sheared off, or otherwise captured inside the hollow portion 146 of the harvester tube 140. This may be accomplished by rotating the harvester tube 140 in a first direction to capture portions of the soft bony tissue inside the hollow portion 146 of the harvester tube 140. More specifically, this may be accomplished by rotating the slide hammer 150 in the first direction with the mechanical stop engaged causing the harvester tube 140 to also rotate in the first direction with the slide hammer 150. The user may also rotate the harvester tube with a slight "rocking" back-and-forth action to enhance the cutting action of the at least one cutting surface 148 disposed at the distal end 144 of the harvester tube 140.

Once the soft bony tissue has been captured inside the hollow portion 146 of the harvester tube 140, the method 800 may proceed to a step 880 in which the slide hammer 150 may be decoupled from the harvester tube 140 in preparation for removal of the harvester tube 140 from the bone. This may be accomplished by rotating the slide hammer 150 in a second direction about the harvester tube 140 to disengage the mechanical stop and decouple the slide hammer 150 from the harvester tube fitting 130. Where the third attachment feature 133 of the harvest tube fitting 130 and the second attachment feature 151 of the slide hammer 150 each consist of threading, as shown in FIGS. 5D and 7B, this step may entail unscrewing the second attachment feature 151 of the slide hammer 150 from the third attachment feature 133 of the harvest tube fitting 130. In at least one embodiment, two torque apertures 135 may be used to receive an appropriate torque tool (not shown) to enable the user to hold the harvester tube fitting 130 steady while applying a rotational force to the slide hammer 150 in the second direction to disengage the mechanical stop and decouple the slide hammer 150 from the harvester tube fitting 130.

Once the slide hammer 150 has been decoupled from the harvester tube fitting 130 and the slide hammer 150 is free to translate along the harvester tube 140, the method 800 may proceed to a step 890 in which the slide hammer 150 may be translated proximally to impart a second impact force on the harvester tube fitting 130 to remove the harvester tube 140 from the bone. In at least one embodiment, the hammer insert 160 may be used to help transmit the second impact force from the slide hammer 150 to the harvester tube fitting 130. More specifically, the hammer insert 160 may be placed intermediate the slide hammer 150 and the harvester tube fitting 130 and the user may translate the slide hammer 150 toward the hammer insert 160 striking the distal end 164 of the hammer insert 160 with the proximal end 152 (or the third impact surface 158) of the slide hammer 150. The second impact force may be transmitted through the hammer insert 160 to the proximal end 162 of the hammer insert 160, and then transmitted to the second impact surface 139 of the harvester tube fitting 130. In the alternative, the hammer insert 160 may be secured to the slide hammer 150 during translation of the slide hammer 150 along the harvester tube 140, as described previously.

Once the harvester tube 140 has been removed from the bone, the method 800 may proceed to a step 892 in which the plunger 120 may be reinserted into the harvester tube 140 to push out bone tissue that has been captured in the hollow portion 146 of the harvester tube 140 to harvest the bone. Once the bone has been harvested, the method 800 may proceed to a step 894 in which the surgical wound above the bone harvest site may be closed. This may be carried out through the use of methods known in the art. The method 800 may then end 898.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it will be appreciated that in the above description of embodiments, various features are sometimes grouped together in a single embodiment, figure, or description for the purpose of streamlining the disclosure. This method of disclosure, however, is not to be interpreted as reflecting an intention that any claim in this or any application claiming priority to this application require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Only elements recited in means-plus-function format are intended to be construed in accordance with 35 U.S.C. § 112 Para. 6. It will be apparent to those having skill in the art that changes may be made to the details of the above-described embodiments without departing from the underlying principles disclosed herein.

While specific embodiments and applications have been illustrated and described, it is to be understood that the appended claims are not limited to the precise configuration and components disclosed herein. Various modifications, changes, and variations which will be apparent to those skilled in the art may be made in the arrangement, operation, and details of the systems and methods disclosed herein without departing from the spirit and scope of the disclosure.

What is claimed is:

1. A device for harvesting bone, the device comprising:
    a harvester tube, the harvester tube comprising:
        a proximal end;
        a distal end; and
        a hollow portion intermediate the proximal end and the distal end, wherein the hollow portion is configured to receive a sample of a bone therein;
    a harvester tube fitting coupled to the proximal end of the harvester tube, the harvester tube fitting comprising a harvester tube fitting impact surface; and
    a slide hammer configured to translate along the harvester tube, wherein the slide hammer comprises a slide hammer impact surface positioned to impact the harvest tube fitting impact surface in response to translation of the slide hammer toward the proximal end to urge removal of the proximal end from the bone;
    wherein:
        the harvester tube fitting comprises a first attachment feature; and
        the slide hammer comprises a second attachment feature configured to detachably couple the slide hammer to the first attachment feature of the harvester tube fitting to selectively prevent the slide hammer from translating along the harvester tube.

2. The device of claim 1, wherein the first attachment feature and the second attachment feature comprise complementary mechanical threading.

3. The device of claim 2, wherein:
    the harvester tube fitting impact surface of the harvester tube fitting defines a mechanical stop that prevents the slide hammer from rotating about the harvester tube in a first direction when the slide hammer engages the mechanical stop; and
    the harvester tube fitting and the slide hammer are configured such that rotating the slide hammer about the harvester tube in a second direction disengages the slide hammer from the mechanical stop.

4. The device of claim 3, wherein:
    the harvester tube fitting further comprises one or more torque features configured to receive a first torque force to facilitate rotation of the slide hammer about the harvester tube in the first direction and a second torque force to facilitate rotation of the slide hammer about the harvester tube in the second direction; and
    the one or more torque features comprise two torque apertures formed on a proximally-facing surface of the harvester tube fitting.

5. The device of claim 1, wherein:
    the harvester tube fitting further comprises a first impact surface and the harvester tube fitting impact surface comprises a second impact surface; and
    the first impact surface is configured to receive an impact force that urges the distal end of the harvester tube into the bone.

6. The device of claim 5, further comprising a hammer insert positionable intermediate the slide hammer and the harvester tube fitting;
    wherein the hammer insert is configured to receive impact from the slide hammer and transmit the impact to the second impact surface of the harvester tube fitting.

7. The device of claim 1, further comprising a plunger, the plunger comprising:
    a proximal end; and
    a distal end comprising a point configured to broach cortical bone;
    wherein the hollow portion of the harvester tube is configured to slidably receive the plunger therein.

8. The device of claim 7, further comprising an end cap coupled to the proximal end of the plunger, the end cap comprising a fourth impact surface configured to receive an impact force and transmit the impact force to a proximally-facing surface of the harvester tube fitting; wherein the harvester tube fitting further comprises a third attachment feature and the end cap comprises a fourth attachment feature configured to detachably couple the plunger to the harvester tube fitting to selectively prevent the plunger from sliding within the hollow portion of the harvester tube.

9. The device of claim 1, wherein the slide hammer comprises a handle portion comprising a knurled surface that improves gripping friction.

10. The device of claim 1, wherein the harvester tube further comprises at least one cutting surface positioned at the distal end of the harvester tube.

11. The device of claim 1, wherein the harvester tube further comprises one or more depth gauges that indicate a depth to which the distal end of the harvester tube has been inserted into the bone.

12. A device for harvesting bone, the device comprising:
a plunger comprising:
 a proximal end; and
 a distal end comprising a point configured to broach cortical bone;
a harvester tube, the harvester tube comprising:
 a proximal end;
 a distal end; and
 a hollow portion intermediate the proximal end and the distal end, wherein the hollow portion is configured to slidably receive the plunger therein, and is further configured to receive a sample of a bone therein;
a harvester tube fitting coupled to the proximal end of the harvester tube, the harvester tube fitting comprising:
 a first impact surface configured to receive a first impact force that urges the distal end of the harvester tube into the bone;
 a second impact surface; and
 a first attachment feature; and
a slide hammer configured to translate along the harvester tube, wherein the slide hammer comprises:
 a slide hammer impact surface positioned to impact the second impact surface in response to translation of the slide hammer toward the proximal end to urge removal of the proximal end from the bone; and
 a second attachment feature configured to detachably couple the slide hammer to the first attachment feature of the harvester tube fitting to selectively prevent the slide hammer from translating along the harvester tube.

13. A device for harvesting bone, the device comprising:
a harvester tube, the harvester tube comprising:
 a proximal end;
 a distal end; and
 a hollow portion intermediate the proximal end and the distal end, wherein the hollow portion is configured to receive a sample of a bone therein;
a harvester tube fitting coupled to the proximal end of the harvester tube, the harvester tube fitting comprising a harvester tube fitting impact surface; and
a slide hammer configured to translate along the harvester tube, wherein the slide hammer comprises a slide hammer impact surface positioned to impact the harvest tube fitting impact surface in response to translation of the slide hammer toward the proximal end to urge removal of the proximal end from the bone;

wherein:
 the harvester tube fitting further comprises a first impact surface and the harvester tube fitting impact surface comprises a second impact surface;
 the first impact surface is configured to receive an impact force that urges the distal end of the harvester tube into the bone;
 the device further comprises a hammer insert positionable intermediate the slide hammer and the harvester tube fitting; and
 the hammer insert is configured to receive impact from the slide hammer and transmit the impact to the second impact surface of the harvester tube fitting.

14. The device of claim 13, further comprising a plunger, the plunger comprising:
a proximal end; and
a distal end comprising a point configured to broach cortical bone;
wherein the hollow portion of the harvester tube is configured to slidably receive the plunger therein.

15. The device of claim 14, further comprising an end cap coupled to the proximal end of the plunger, the end cap comprising a fourth impact surface configured to receive an impact force and transmit the impact force to a proximally-facing surface of the harvester tube fitting;
wherein the harvester tube fitting further comprises a third attachment feature and the end cap comprises a fourth attachment feature configured to detachably couple the plunger to the harvester tube fitting to selectively prevent the plunger from sliding within the hollow portion of the harvester tube.

16. The device of claim 12, wherein the first attachment feature and the second attachment feature comprise complementary mechanical threading.

17. The device of claim 16, wherein:
the harvester tube fitting impact surface of the harvester tube fitting defines a mechanical stop that prevents the slide hammer from rotating about the harvester tube in a first direction when the slide hammer engages the mechanical stop; and
the harvester tube fitting and the slide hammer are configured such that rotating the slide hammer about the harvester tube in a second direction disengages the slide hammer from the mechanical stop.

18. The device of claim 17, wherein:
the harvester tube fitting further comprises one or more torque features configured to receive a first torque force to facilitate rotation of the slide hammer about the harvester tube in the first direction and a second torque force to facilitate rotation of the slide hammer about the harvester tube in the second direction; and
the one or more torque features comprise two torque apertures formed on a proximally-facing surface of the harvester tube fitting.

19. The device of claim 12, wherein:
the harvester tube fitting further comprises a first impact surface and the harvester tube fitting impact surface comprises a second impact surface;
the first impact surface is configured to receive an impact force that urges the distal end of the harvester tube into the bone;
the device further comprises a hammer insert positionable intermediate the slide hammer and the harvester tube fitting; and
the hammer insert is configured to receive impact from the slide hammer and transmit the impact to the second impact surface of the harvester tube fitting.

20. The device of claim 12, further comprising:
a plunger, the plunger comprising:
- a proximal end; and
- a distal end comprising a point configured to broach cortical bone; and an end cap coupled to the proximal end of the plunger;
wherein:
- the hollow portion of the harvester tube is configured to slidably receive the plunger therein;
- the end cap comprises a fourth impact surface configured to receive an impact force and transmit the impact force to a proximally-facing surface of the harvester tube fitting; and
- the harvester tube fitting further comprises a third attachment feature and the end cap comprises a fourth attachment feature configured to detachably couple the plunger to the harvester tube fitting to selectively prevent the plunger from sliding within the hollow portion of the harvester tube.

* * * * *